US005908624A

United States Patent [19]
Scott et al.

[11] Patent Number: 5,908,624
[45] Date of Patent: Jun. 1, 1999

[54] ANTIGENIC MODULATION OF CELLS

[75] Inventors: Mark D. Scott, Clifton Park, N.Y.; John W. Eaton, Houston, Tex.

[73] Assignee: Albany Medical College, Albany, N.Y.

[21] Appl. No.: 08/671,452

[22] Filed: Jun. 27, 1996

[51] Int. Cl.$^6$ .......................... A61K 35/12; A61K 35/39; C12N 5/00

[52] U.S. Cl. .................... 424/93.7; 424/93.1; 424/184.1; 435/325; 435/382; 435/177; 435/178; 435/181; 435/1.1

[58] Field of Search .................................. 424/93.7, 93.1, 424/184.1; 435/325, 382, 177, 178, 181, 1.1

[56] References Cited

U.S. PATENT DOCUMENTS

| | | |
|---|---|---|
| 4,179,337 | 12/1979 | Davis et al. . |
| 5,006,333 | 4/1991 | Saifer et al. . |
| 5,013,556 | 5/1991 | Woodle et al. . |
| 5,214,131 | 5/1993 | Sano et al. . |
| 5,380,536 | 1/1995 | Hubbell et al. . |
| 5,395,619 | 3/1995 | Zalipsky et al. . |
| 5,399,665 | 3/1995 | Barrera et al. . |
| 5,529,914 | 6/1996 | Hubbel et al. . |
| 5,578,442 | 11/1996 | DeSai et al. ............................. 435/1.1 |

FOREIGN PATENT DOCUMENTS

95/06058  2/1995  WIPO .

OTHER PUBLICATIONS

Lim et al., "Microencapsulated Islets as Bioartificial Endocrine Pancreas", *Science*, vol. 210, pp. 908–910, (Nov. 21, 1980).

Abraham Abuchowski, et al., "Alteration of Immunological Properties of Bovine Serum Albumin by Covalent Attachment of Polyethylene Glycol", *The Journal of Biological Chemistry*, vol 252, No. 11, pp. 3578–3581, (June 10, 1997).

Abraham Abuchowski, et al., "Effect of Covalent Attachment of Polyethylene Glycol on Immunogenicity and Circulating Life of bovine Liver Catalase", *The Journal of Biological Chemistry*, vol 252, No. 11, pp. 3582–3586, (June 10, 1977).

J. Milton Harris, "Laboratory Synthesis of Polyethylene Glycol Derivatives", *Macromol. Chem. Phys.,*, C25 (3), pp. 325–373, (1985).

J. Milton Harris et al., "Synthesis and Characterization of Poly(ethylene glycol) Derivatives", *Journal of Polymer Science, Polymer Chemistry Edition*, vol. 22, pp. 341–352, (1984).

C. Anthony Hunt, et al., "Synthesis and Evaluation of a Prototypal Artificial Red Cell", *Science*, Vol. 230, pp. 1165–1168, (Dec. 6, 1985).

Chung–Ja C. Jackson, et al., "Synthesis, Isolation, and Characterization of Conjugates of Ovalbumin with Monomethoxypolyethylene Glycol Using Cyanuric Chloride as the Coupling Agent", *Analytical Biochemistry*, 165, pp. 114–127, (1987).

Aleksander L. Klibanov, et al., "Activity of amphipathic poly(ethylene glycol) 5000 to prolong the circulation of time of liposomes depends on the liposome size and is unfaavorabale for immunoliposome binding to target", *Biochimica et Biophysica Acta*, 1062, pp. 142–148, (1991).

Paul E. Lacy, et al., "Maintenance of Normoglycemia in Diabetic Mice by Subcutaneous Xemografts of Encapsulated Islets", *Science*, vol. 254, pp. 1782–1784, (1991).

Danilo Lasic, "Liposomes–Synthetic lipid microspheres serve as multipurpose vehicles for the delivery of drugs, genetic material and cosmetics", *American Scientist*, vol. 80, pp. 20–31, (Jan.–Feb. 1992).

Kazuo Maruyama, et al., "Prolonged circulation time in vivo of large unilamellar liposomes composed of distearoyl phosphatidycholine and chlosterol containing amphipathic poly–(ethylene glycol)", *Biochimica et Biophysica Acta*, 1128, pp. 44–49, (1992).

Edward W. Merrill, "Poly(Ethylene Oxide) and Blood Contact, a Chronicle of ONe Laboratory", 14.1, pp. 199–220, (1992).

Ki Dong Park, et al., "PEO–Modified surfaces–In Vitro, Ex Vivo, and In Vivo Blood Compatability", pp. 283–300, (1992).

Amarpreet S. Sawhney, et al., "Modification of Islet of Langerhans surfaces with Immunoprotective Poly(ethylene glycol) Coatings via Interfacial Photopolymerization", *Biotechnology and Bioengineering*, vol. 44, pp. 383–386, (1994).

Judith Senior, et al., "Influence of surface hydrophilicity of liposomes on their interaction with plasma protein and clearance from the circulation: studies with poly(ethylene glycol coated vesicles", *Biochimica et Biophysica Acta*, 1062, pp. 77–82, (1991).

Samuel Zalipsky, et al., "Use of Functionalized Poly(ethylene Glycols) for Modificationof polypeptides", 21.1 Introduction, In Poly(Ethylene Glycol) Chemistry: Biotechnical and Biomedical Applications (ed. J. Milton Harris) Plenum Press, New York (1992). pp. 347–370.

*Primary Examiner*—Anthony C. Caputa
*Assistant Examiner*—Robert C. Hayes
*Attorney, Agent, or Firm*—Schwegman, Lundberg, Woessner, and Kluth, P.A.

[57] ABSTRACT

The present invention is directed to a non-immunogenic cellular composition comprising: a cell having a cell surface and antigenic determinants on the cell surface; a linker molecule covalently attached to the cell surface; and a non-immunogenic compound (e.g., polyethylene glycol or derivative thereof) covalently attached to the linker molecule. In one embodiment, the linker molecule is covalently attached directly to the antigenic determinant on the cell surface. In an alternate embodiment, the linker molecule may be covalently attached to a non-antigenic site on the cell surface, but will camouflage the antigenic determinant on the cell surface by virtue of the long chain length of the non-immunogenic compound. Various uses of the resulting non-immunogenic cell are also provided, including a method of decreasing phagocytosis of a cell, a method of decreasing an adverse reaction to a transfusion, a method of decreasing rejection of a transplanted cell, tissue or organ, and a method of decreasing antibody-induced aggregation of cells.

20 Claims, 8 Drawing Sheets

= ACTIVATED PEG

◯ = ANTIGENIC SITE

⬭ = ANTIGENIC SITE

FIG. 2

ANTIGENIC MODULATION OF CELLS

The subject matter of this application was made with support from the United States Government under grant HL53066 of the National Institutes of Health.

FIELD OF THE INVENTION

The present invention relates generally to antigenic modulation of cells, and more particularly to non-immunogenic cellular compositions comprising cells modified with a non-immunogenic compound, and uses of such non-immunogenic cells.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Acute tissue rejection can be observed in two major clinical situations: 1) blood transfusions; and 2) organ transplantation. In both situations, to be described in greater detail below, antibody binding and complement fixation are the two major mechanisms underlying the destruction of the donor tissue (the donor tissue referring to blood or organs). Previous means of attempting to control acute rejection have centered on tissue matching and pharmacologic interventions. Despite these measures a significant number of often life-threatening acute tissue rejection reactions continue to occur.

Blood transfusions are a crucial component in the treatment of a number of acute and chronic medical problems. These range from massive blood loss following traumatic injury to chronic transfusions in diseases such as thalassemia and sickle cell anemia. In most acute injuries simple blood typing (ABO/rh) is sufficient to identify appropriate donors. Occasionally, however, rare blood types are encountered where an appropriate match cannot be quickly found, a situation which may be life-threatening. More often problems are encountered in individuals, usually minorities, receiving chronic transfusions (e.g., as in sickle cell anemia and the thalassemias). Often simple blood typing becomes insufficient in determining a proper match because these individuals develop transfusion reactions to minor red blood cell antigens. The transfusion reactions to these minor red blood cell antigens can make it nearly impossible to identify appropriate blood donors (Vichinsky et al. 1990).

To date, the only solutions to the above situations are to store autologous blood (frozen or at 4° C.), keep a blood bank registry of potential donors with rare blood types, and to encourage minority blood donations. While all of these steps are prudent and variably effective, situations still arise where an appropriate (or even satisfactory) blood match cannot be made. Therefore, a need exists for methods and agents which will disguise otherwise immunogenic (or directly immunologically recognizable) red blood cells.

Similarly, the transplantation of organs (such as kidneys and livers) from one human to another is often made difficult by a lack of exact immunologic identity between donor and recipient. Sometimes, the transplanted organ is subject to direct attack by the immune system of the recipient even before a secondary immunologic response has had time to occur. This so-called 'hyperacute rejection' is often life threatening and, obviously, prevents the effective integration of the transplant into the recipient. Therefore, a need exists for methods and agents which may prevent immediate recognition of the endothelial surfaces of organ transplants, thereby moderating or stopping the process of acute graft rejection. In a similar vein, the transplantation of organs from one species to another ('xenotransplant') faces even more formidable immunologic barriers and would be greatly facilitated by methods for blocking immunologic recognition of the foreign endothelial surface.

Proteins have been modified by the covalent attachment of soluble polymers such as polyvinyl alcohol, carboxymethyl cellulose (Mitz and Summaria 1961), and polyvinylpyrrolidone (von Specht et al. 1973). Various antigenic purified proteins have also been modified by covalent attachment of polyethylene glycols (PEGs) to render the resulting proteins non-immunogenic. Abuchowski et al. (1977a) disclose the modification of purified bovine serum albumin (BSA) by covalent attachment of methoxypolyethylene glycol, rendering the BSA non-immunogenic. Abuchowski et al. (1977b) disclose the modification of purified bovine liver catalase by covalent attachment of methoxypolyethylene glycol, rendering the catalase non-immunogenic. Jackson et al. (1987) disclose the modification of purified ovalbumin with monomethoxypolyethylene glycol using cyanuric chloride as a coupling agent. The resulting ovalbumin is non-immunogenic.

Various reports have also shown that polyethylene glycol (PEG) coated liposomes have improved circulation time (Klivanov et al. 1991; Senior et al. 1991; Maruyama et al. 1992; and Lasic 1992).

Islet of Langerhans have been microencapsulated in semipermeable membranes in order to decrease immunogenicity of implanted islets (Lacy et al. 1991; Lim 1980). Sawhney et al. (1994) coated rat islets with a polyethylene glycol tetraarylate hydrogel. Importantly, PEG was not directly incorporated into the islet cell membranes but rather the cells were surrounded by the PEG-containing hydrogel.

Zalipsky and Lee (1992) discuss the use of functionalized polyethylene glycols for modification of polypeptides, while Merrill (1992) and Park and Wan Kim (1992) both relate to protein modification with polyethylene oxide.

U.S. Pat. No. 4,179,337 of Davis et al. discloses purified polypeptides, such as enzymes and insulin, which are coupled to polyethylene glycol or polypropylene glycol having a molecular weight of 500 to 20,000 daltons to provide a physiologically active non-immunogenic water soluble polypeptide composition. The polyethylene glycol or polypropylene glycol protect the polypeptide from loss of activity and the composition can be injected into the mammalian circulatory system with substantially no immunogenic response.

U.S. Pat. No. 5,006,333 of Saifer et al. discloses a biologically persistent, water-soluble, substantially non-immunogenic, substantially non-antigenic conjugate of superoxide dismutase, prepared by coupling purified superoxide dismutase to one to five strands of a polyalkylene glycol which is polyethylene glycol or polyethylene-polypropylene glycol copolymer, wherein the polyalkylene glycol has an average molecular weight of about 35,000–1,000,000.

U.S. Pat. No. 5,013,556 of Woodle et al. discloses a liposome composition which contains between 1–20 mole percent of an amphipathic lipid derivatized with a polyalkylether, as exemplified by phosphatidylethanolamine derivatized with polyethylene glycol.

U.S. Pat. No. 5,214,131 of Sano et al. discloses a polyethylene glycol derivative, a purified peptide modified by the polyethylene glycol derivative, and a method for production thereof. The polyethylene glycol derivative is capable of modifying the guanidino groups in peptides. The peptides modified by the polyethylene glycol derivative are extremely stable, are considerably delayed in biological clearance, and exhibit their physiological activities effectively over a long period.

A need continues to exist for methods of making entire cells and tissues and organs, as opposed to purified proteins or peptides, non-immunogenic.

SUMMARY OF INVENTION

To this end, the subject invention provides for the covalent binding of a non-immunogenic compound to intact cells. The invention is useful in modulating the antigenicity and aggregation of cells. In one embodiment, the non-immunogenic compound is polyethylene glycol (PEG) or a derivative thereof. These PEG-modified cells have normal in vitro and in vivo survival when compared to control cells. Potential applications for PEG modification of cells include: 1) PEG-derivatized red blood cells to diminish transfusion reactions arising from mismatched blood or sensitization to minor blood group antigens due to chronic transfusions; 2) PEG-derivitization of the vascular endothelium of donor tissues prior to transplantation to prevent/diminish acute tissue rejection; and 3) implantation of PEG-derivitized cells to correct enzyme deficiencies, other inborn errors of metabolism, or other types of defective cellular functions.

Covalent linkage of non-immunogenic compounds (e.g., PEG or PEG-derivatives, such as methoxypolyethylene glycol or PEG-like compounds such as polyethylene oxide), to membrane proteins of cells decreases the antigenic nature of these cells (FIG. 1). Similarly, insertion of PEG-modified phospholipids/free fatty acids into the cell membrane may serve a similar purpose. The subject invention shows that (1) it is possible to derivatize normal red blood cells with PEG, (2) that the derivatized cells remain intact (3) that PEG modification of the cell surface does, indeed, 'hide' antigenic determinants such as ABO blood groups, (4) that the derivatized cells survive normally in the circulation of experimental animals, and (5) that PEG derivatized red blood cells from one species have vastly improved survival in the circulation of an animal from another species.

As delineated above, transfusion reactions (to both major and minor red blood cell antigens) represent a significant clinical problem. In most cases, these transfusion reactions actually result from minor surface antigens not typically measured by blood banks. In situations where either an appropriate blood type match can not be located or, more often, when sensitization to minor red blood cell antigens has occurred, PEG-modified red blood cells can be employed to diminish/prevent the recognition of red blood cell antigenic determinants. The application of this invention can also lead to procedures for modification of animal red blood cells which can then be used for transfusion into humans. The application of this invention can further lead to procedures for modification of red blood cells to prevent malarial invasion or opsonization by factors such as complement.

In addition, based on the data contained in this disclosure, the scope of this invention extends well beyond blood banking to other areas where foreign tissues are introduced. One area of primary interest is the use of PEG-modified tissues (especially covalent modification of the vascular endothelium) for tissue transplantation. Despite appropriate HLA-matches, many organ transplants fail as a result of immediate tissue rejection. This rejection reaction occurs primarily at the level of the vascular endothelium and results in vessel occlusion, tissue hypoxia/ischemia and ultimate loss of the organ transplant. Based on the chemistry of PEG-cell derivatization disclosed herein, it is possible to perfuse the vasculature of the tissue with a solution of activated PEG. This will modify the vessel walls (i.e., endothelial cells) which will prevent or diminish the aforementioned immediate tissue rejection. This technology can thus improve the rate of successful tissue engraftment.

The invention thus provides a non-immunogenic cellular composition comprising: a cell having a cell surface and antigenic determinants on the cell surface; a linker molecule covalently attached to the cell surface; and a non-immunogenic compound covalently attached to the linker molecule and capable of blocking recognition of the antigenic determinants on the cell surface. In one embodiment, the linker molecule is covalently attached directly to the antigenic determinant on the cell surface. In an alternate embodiment, the linker molecule may be covalently attached to a non-antigenic site of the cell surface, but will camouflage the antigenic site on the cell surface by virtue of the long chain length of the non-immunogenic compound.

The invention further provides a method of producing a non-immunogenic cell. The method comprises: covalently attaching a non-immunogenic compound to a linker molecule, the non-immunogenic compound capable of blocking recognition of antigenic determinants on a cell surface; and covalently attaching the linker molecule to a cell surface, so as to produce a non-immunogenic cell. A non-immunogenic cell produced by this method is also provided by the subject invention.

The concept of the subject invention can also provide a method of decreasing phagocytosis of a cell. This method comprises: selecting a cell for introduction into a subject, the cell having a cell surface and antigenic determinants on the cell surface; covalently attaching a non-immunogenic compound to a linker molecule, the non-immunogenic compound capable of blocking recognition of the antigenic determinants on the cell surface; covalently attaching the linker molecule to the cell surface, so as to produce a non-immunogenic cell; and introducing the non-immunogenic cell into a subject, wherein phagocytosis of the non-immunogenic cell is decreased as compared to phagocytosis of the cell prior to modification.

Further provided is a method of decreasing an adverse reaction to a transfusion, the method comprising: selecting a red blood cell for transfusion into a subject, the red blood cell having a cell surface and blood group antigenic determinants on the cell surface; covalently attaching a non-immunogenic compound to a linker molecule, the non-immunogenic compound capable of blocking the blood group antigenic determinants on the cell surface; covalently attaching the linker molecule to the cell surface, so as to produce a non-immunogenic red blood cell; and transfusing a subject with the non-immunogenic red blood cell, wherein adverse reaction to the transfusion of the non-immunogenic red blood cell is decreased as compared to transfusion of the red blood cell prior to modification.

Also provided is a method of decreasing rejection of a transplanted cell, the method comprising: selecting a cell for transplantation into a subject, the cell having a cell surface and antigenic determinants on the cell surface; covalently attaching a non-immunogenic compound to a linker molecule, the non-immunogenic compound capable of blocking the recognition of the antigenic determinants on the cell surface; covalently attaching the linker molecule to the cell surface, so as to produce a non-immunogenic cell; and transplanting the non-immunogenic cell into a subject, wherein rejection of the transplanted cell is decreased as compared to rejection of the cell prior to modification.

The invention provides a method of decreasing antibody-induced aggregation of cells, the method comprising: covalently attaching non-immunogenic compounds to linker molecules, the non-immunogenic compounds capable of blocking recognition of antigenic determinants on a cell surface; and covalently attaching one of said linker molecules to the cell surface of each of a plurality of cells, so as to produce non-aggregating cells, wherein antibody-induced aggregation of the non-aggregating cells is decreased as compared to antibody-induced aggregation of the cells prior to modification.

BRIEF DESCRIPTION OF THE FIGURES

These and other features and advantages of this invention will be evident from the following description of preferred embodiments when read in conjunction with the accompanying drawings in which:

FIG. 1 shows the structure of one embodiment of a non-immunogenic cellular composition according to the subject invention;

Figure 2:
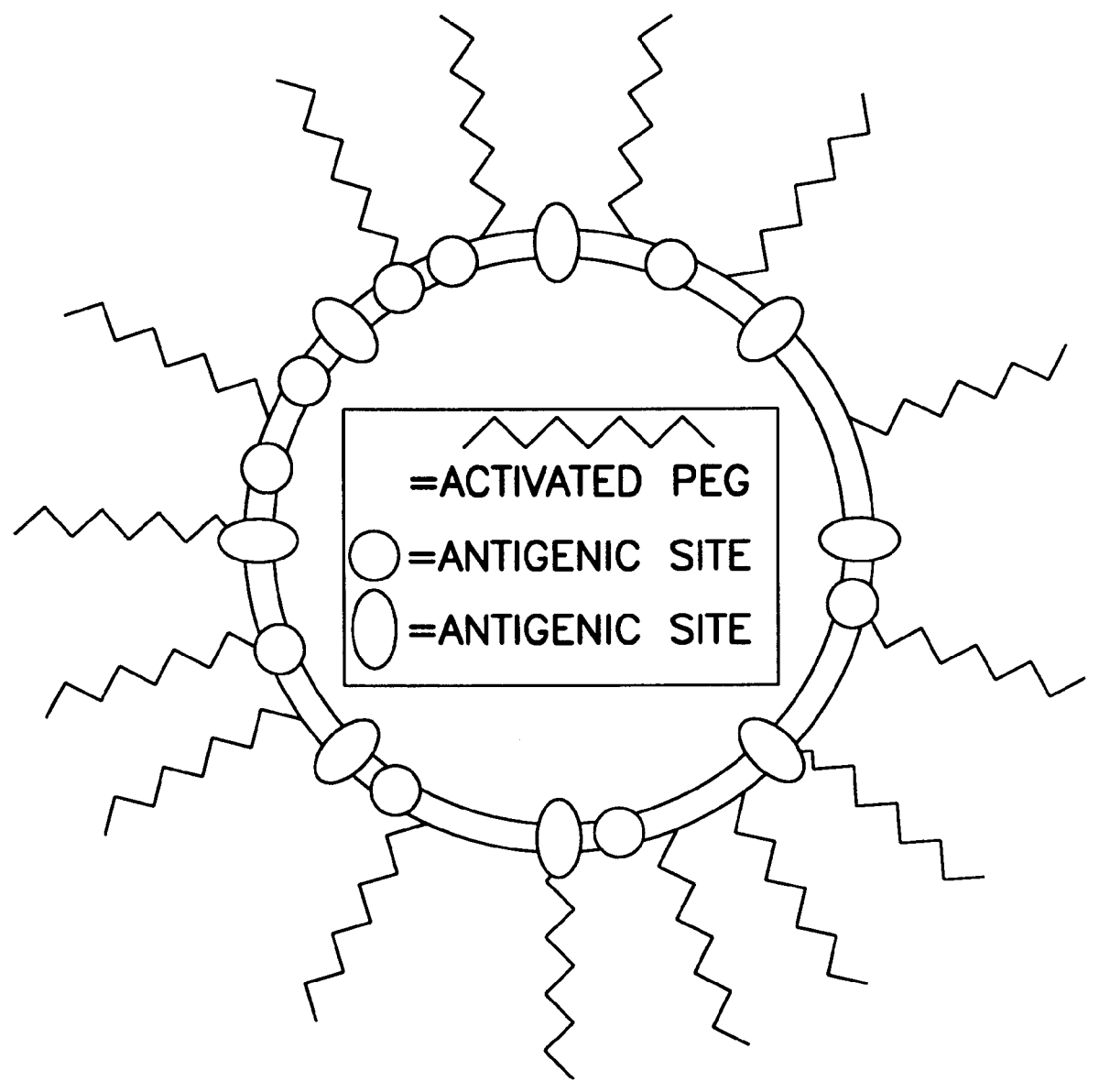

FIG. 2 shows the structure of a further embodiment of a non-immunogenic cellular composition according to the subject invention. In this embodiment, the non-immunogenic compound is polyethylene glycol or a derivative thereof and the activated PEG (PEG-linker) is covalently attached to antigenic determinants on the cell surface (directly blocking antigenic sites) and also covalently attached to non-antigenic sites on the cell surface (indirectly blocking antigenic sites due to their long chain length);

FIG. 3 is a graph showing that monomethoxypoly (ethylene glycol) (mPEG) modification of red blood cells causes a dose-dependent inhibition of anti-A antibody induced RBC aggregation defined turbidometrically;

FIG. 4 is a bar graph showing that mPEG modification of red blood cells only slightly increases red blood cell lysis;

FIG. 5 is a graph showing the mPEG modification of red blood cells has no effect on red blood cell osmotic fragility;

FIG. 6 is a bar graph showing that mPEG-modified type A red blood cells bind significantly less anti-A antibody;

FIG. 7 is a bar graph showing that mPEG-modified sheep red blood cells are significantly less prone to phagocytosis by human peripheral blood monocytes;

FIG. 8 is a graph showing no significant differences in the in vivo survival of control mouse red blood cells and mouse red blood cells modified with activated PEG; and FIG. 9 is a graph demonstrating that sheep red blood cells (solid symbols) enter and survive within the circulatory system of a mouse whereas unmodified sheep red blood cells (open symbols) do not.

DETAILED DESCRIPTION

The subject invention provides a non-immunogenic cellular composition comprising: a cell having a cell surface and antigenic determinants on the cell surface; a linker molecule covalently attached to the cell surface; and a non-immunogenic compound covalently attached to the linker molecule and capable of blocking recognition of the antigenic determinants on the cell surface.

The cell can be any suitable cell with antigenic determinants on the cell's surface. Suitable cells include anuclear cells, for example red blood cells or platelets, or nucleated cells, for example, vascular endothelial cells, hepatic cells, neuronal cells, pancreatic cells, or epithelial cells. These various exemplified anuclear cells and nucleated cells are examples only, and the invention is not intended to be limited to these particular examples.

The antigenic determinants on the cell surface can be due to the presence of antigenic proteins, antigenic carbohydrates, antigenic sugars, antigenic lipids, antigenic glycolipids, antigenic glycoproteins, etc. "Antigenic" determinants can also be involved in malarial invasion of a cell, or opsonization of a cell. For example, red blood cells have antigens on their surface which determine ABO/rh blood types. These antigens are often referred to as blood group antigenic determinants. These antigens are recognized by an incompatible host and the donor cell will be rapidly destroyed. This can involve the enhancement of natural immunity (through phagocytes, such as macrophages, neutrophils, and natural killer cells) or the stimulation of specific or acquired immunity (including humoral immunity through antibodies and cell-mediated immunity through T lymphocytes). In any event, the cell is recognized as foreign and elicits an immune response.

In order to prevent this immune response from destroying the cell, the subject invention modifies the antigenicity of the cell. This modification is accomplished by attaching a non-immunogenic compound to the cell. Suitable non-immunogenic compounds for use in the subject invention are non-immunogenic compounds capable of blocking recognition of antigenic determinants on the cell surface. The compounds are generally long chain compounds and the long chain sterically blocks the antigenic determinants. Such non-immunogenic compounds include polyethylene glycol or derivatives thereof (including monomethoxypolyethylene glycol), polyethylene oxide, dextrans, ficoll, and arabinogalactan. Other suitable long chain non-immunogenic compounds should be readily apparent to those skilled in the art.

The presently preferred non-immunogenic compound according to the subject invention is polyethylene glycol or a derivative thereof. The polyethylene glycol or derivative thereof is a molecule with a very long chain length. The non-immunogenic compound (e.g., polyethylene glycol or derivative thereof) can be directly attached to an antigenic site (e.g., an antigenic determinant) on a cell surface via a linker molecule (direct modification of antigenicity) (see FIG. 1 and FIG. 2) or can be attached to a non-antigenic site on the cell surface via a linker molecule. In both cases, the long chain of the non-immunogenic compound (e.g., polyethylene glycol or derivative thereof) effectively blocks antigenic sites on the cell surface (indirect modification of antigenicity) (see FIG. 2). In either embodiment, the non-immunogenic compound (e.g., polyethylene glycol or derivative thereof) is attached to the cell surface by a linker molecule. The combination of a polyethylene glycol or derivative thereof and the linker molecule is generally referred to as an "activated" polyethylene glycol or derivative thereof.

Polyethylene glycols (PEG) and derivatives thereof are well known in the art. Polyethylene glycol has the formula $$H(OCH_2CH_2)_nOH$$

wherein n is greater than or equal to 4, with a molecular weight of up to about 20,000 Daltons. Various derivatives of polyethylene glycol substitute for the H or OH end groups, forming, for example, polyethylene glycol ethers (such as PEG—O—R; PEG—O—$CH_3$; $CH_3$—PEG—OH or "mPEG"; 2,4-dinitrophenyl ethers of PEG), polyethylene glycol esters (such as PEG—$O_2C(CH_2)_{14}CH_3$; PEG—$O_2CCH_2CH_2CO_2$-atropine), polyethylene glycol amides (such as PEG—$O_2C(CH_2)_7CONHR$; mPEG—$O_2CCH_2CH_2CONH(CH_3)CHCH_2C_6H_5$; PEG—$O_2CCH_2CH_2CONHCH_2CH_2$—$NAD^+$), polyethylene glycol amines (such as PEG—$NH_2$; PEG—$NH(CH_2)_6NH_2$; PEG—$OCH_2CH_2NH_2$; mPEG—$NH_2$), polyethylene glycol acids (such as PEG—$O_2C(CH_2)_2CO_2H$; PEG—O—$CH_2CO_2H$; PEG—$O_2C$—$(CH_2)_7$—$CO_2H$), polyethylene glycol aldehydes (PEG—O—$CH_2$—CHO), and electrophilic derivatives (such as PEG—Br; PEG—$OSO_2CH_3$; PEG—O). Various phenyl moieties can also be substituted for the H or OH of PEG, such as the 2,4-dinitrophenyl ether of PEG mentioned above).

For a full discussion of polyethylene glycol and derivatives thereof, including the synthesis of the derivatives, see the following references: Harris et al. 1984; Harris 1985; Zalipsky and Lee 1992; Park and Kim 1992; Merrill 1992; and U.S. Pat. Nos. 4,179,337 and 5,214,131, the contents of each of which are incorporated herein by reference. The particular non-immunogenic compounds, including the polyethylene glycol derivatives, listed above are exemplary only, and the invention is not intended to be limited to those particular examples.

Figure 1:
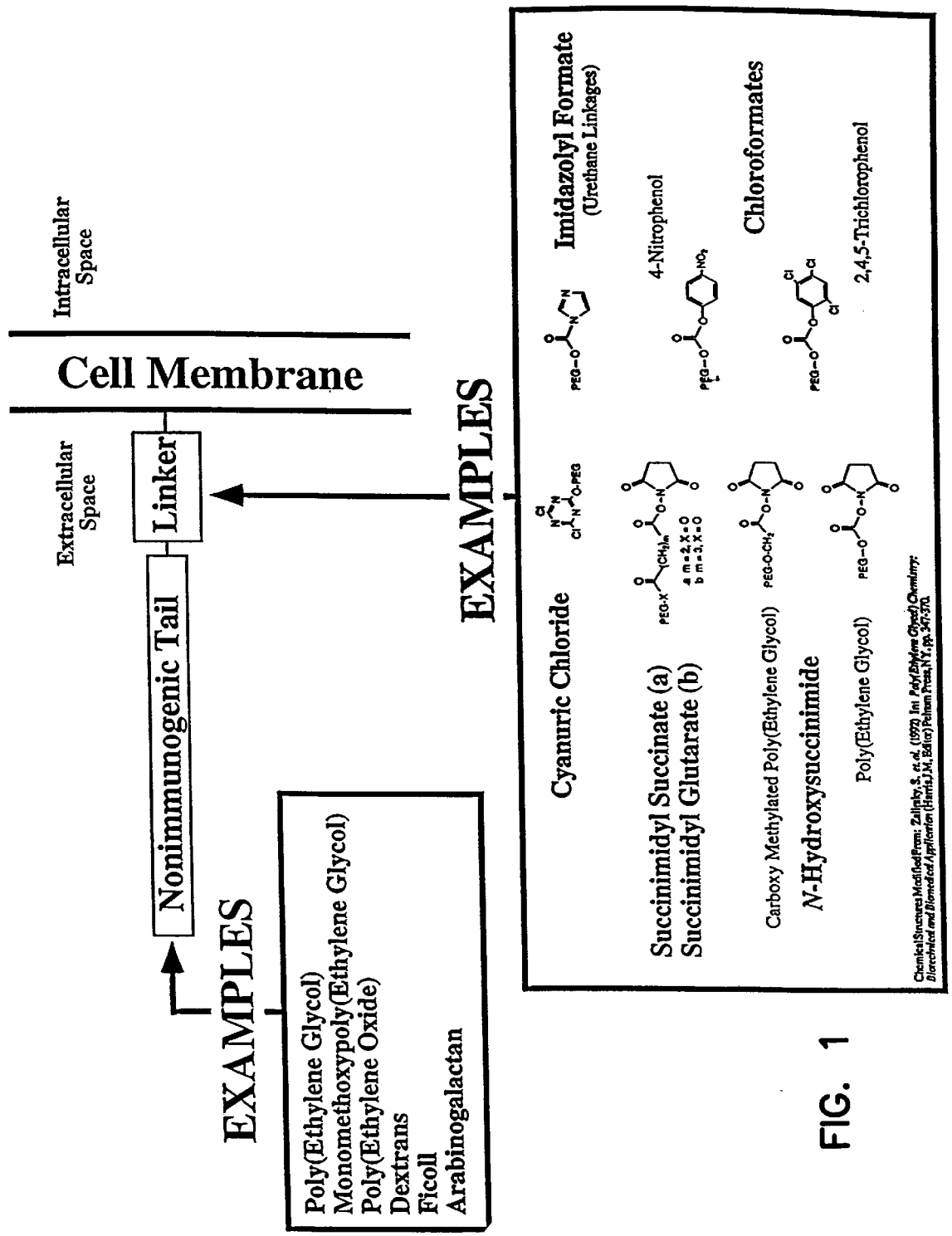

According to the subject invention, these non-immunogenic compounds (e.g., polyethylene glycol molecules or derivatives thereof) are covalently attached to a linker molecule. Suitable linker molecules are also well known in the art, and include, for example, cyanuric chloride, imidazolyl formate, succinimidyl succinate, succinimidyl glutarate, N-hydroxysuccinimide, 4-nitrophenol, and 2,4,5-trichlorophenol. These linker molecules "activate" the PEG, a term also well known in the art. For a description of activation of PEG, with examples of known linkers, see Harris 1985. The linker molecules listed above are exemplary only, and the invention is not intended to be limited to those particular examples. Any linker molecules capable of both covalently attaching to the cell surface and to the non-immunogenic compounds may be similarly used.

The chemistry involved in the covalent attachment of the non-immunogenic compound (such as PEG or a derivative thereof) to the linker molecule, and the covalent attachment of the linker molecule to a cell surface (thus, covalent attachment of the non-immunogenic compound to a cell surface), is known in the art, and is discussed in detail in Harris 1985; Harris et al. 1984; and Zalipsky and Lee 1992. Since polyethylene glycol and its derivatives are very well known in the art, including the synthesis and modification thereof, including attachment to proteins, further details are not disclosed herein relating to this aspect of the invention, other than the examples that follow.

Having thus identified the non-immunogenic cellular composition according to the subject invention, various uses of the invention are possible.

The invention thus further provides a method of producing a non-immunogenic cell. The method comprises: covalently attaching a non-immunogenic compound to a linker molecule, the non-immunogenic compound capable of blocking recognition of antigenic determinants on a cell surface; and covalently attaching the linker molecule to a cell surface, so as to produce a non-immunogenic cell. If the cell is a red blood cell, the method can further comprise transfusing a subject with the non-immunogenic cell. Since the antigenic determinants on the red blood cell are blocked by the non-immunogenic compound, such as the blood group antigenic determinants, the transfused non-immunogenic red blood cell will not elicit an immune response. As discussed above, this method can be very useful when red blood cells need to be transfused quickly without the availability of complete blood typing or cross-matching, or when only blood of a different type from a subject is available.

If the cell is part of a tissue or organ, the method can further comprise transplanting the non-immunogenic tissue or organ into a subject. Since the antigenic determinants on the tissue or organ are blocked by the non-immunogenic compound, such as the vascular endothelial cells which form an exposed antigenic surface of the tissue or organ, the transplanted non-immunogenic tissue or organ will not elicit an immune response. As discussed above, this method is very useful to avoid severe rejection reactions when organs or tissues are transplanted.

The invention further provides a non-immunogenic cell produced by the above method.

The concept of the subject invention can also provide a method of decreasing phagocytosis of a cell. This method comprises: selecting a cell for introduction into a subject, the cell having a cell surface and antigenic determinants on the cell surface; covalently attaching a non-immunogenic compound to a linker molecule, the non-immunogenic compound capable of blocking recognition of the antigenic determinants on the cell surface; covalently attaching the linker molecule to the cell surface, so as to produce a non-immunogenic cell; and introducing the non-immunogenic cell into a subject, wherein phagocytosis of the non-immunogenic cell is decreased as compared to phagocytosis of the cell prior to modification. In the case where the cell is a red blood cell, this method can prevent phagocytosis of the "foreign" red blood cell, by rendering the red blood cell non-immunogenic. The "foreign" red blood cell may be from another human, or may be from another non-human subject. In either case, the body's response would be to attempt to eliminate the "foreign" red blood cell including by phagocytosis.

Further provided is a method of decreasing an adverse reaction to a transfusion, the method comprising: selecting a red blood cell for transfusion into a subject, the red blood cell having a cell surface and blood group antigenic determinants on the cell surface; covalently attaching a non-immunogenic compound to a linker molecule, the non-immunogenic compound capable of blocking the blood group antigenic determinants on the cell surface; covalently attaching the linker molecule to the cell surface, so as to produce a non-immunogenic red blood cell; and transfusing a subject with the non-immunogenic red blood cell, wherein adverse reaction to the transfusion of the non-immunogenic red blood cell is decreased as compared to transfusion of the red blood cell prior to modification. As discussed above, the red blood cell could be from another human or from a non-human subject.

Also provided is a method of decreasing rejection of a transplanted cell, the method comprising: selecting a cell for transplantation into a subject, the cell having a cell surface and antigenic determinants on the cell surface; covalently attaching a non-immunogenic compound to a linker molecule, the non-immunogenic compound capable of blocking the recognition of the antigenic determinants on the cell surface; covalently attaching the linker molecule to the cell surface, so as to produce a non-immunogenic cell; and transplanting the non-immunogenic cell into a subject, wherein rejection of the transplanted cell is decreased as compared to rejection of the cell prior to modification. Where the cell is part of a tissue or organ which is to be transplanted into a subject, a preferred method of carrying out the covalent attachment is to perfuse the tissue or organ with a solution of an activated polyethylene glycol or derivative thereof (i.e., the polyethylene glycol or derivative thereof is first attached to the linker molecule, forming an activated PEG, which is then perfused over the tissue or organ). During the perfusion, the linker portion of the activated PEG covalently attaches to the cell surface.

The invention provides a method of decreasing antibody-induced aggregation of cells, the method comprising: covalently attaching non-immunogenic compounds to linker molecules, the non-immunogenic compounds capable of blocking recognition of antigenic determinants on a cell surface; and covalently attaching one of said linker molecules to the cell surface of each of a plurality of cells, so as to produce non-aggregating cells, wherein antibody-induced aggregation of the non-aggregating cells is decreased as compared to antibody-induced aggregation of the cells prior to modification. This method is particularly applicable where the cells are red blood cells, and where the antigenic determinants on the cell surface comprise blood group antigenic determinants.

In each of the above described methods, the invention is described by attaching a linker molecule to the non-immunogenic compound (forming an "activated" compound) and then attaching the linker to the cell surface. The order of these steps can be reversed, and any reference to the two steps is intended to cover the two steps in either order. Accordingly, the linker molecule can also be attached to the cell surface, then the non-immunogenic compound can be attached to the linker molecule, in accordance with the claims and disclosure herein.

In the examples which follow relating to the preferred embodiment in which the cell is a red blood cell, PEG modification of the external aspect of the red blood cell membrane effectively 'hides' major antigenic determinants such as ABO blood group substances. This is evident in the (1) lack of gross antibody-induced agglutination, (2) significantly decreased antibody-induced aggregation, and (3) diminished phagocytosis by heterologous macrophages. Treated red blood cells remain intact, exhibiting only minor spontaneous hemolysis, and demonstrate normal osmotic fragility over at least 48 hrs in vitro incubation. The "normal" nature of the modified mouse red blood cell is further demonstrated by normal in vivo survival.

The PEG modification procedure is surprisingly well tolerated by the cells, yielding a product which survives normally in the circulation. The derivatized cells are antigenically disguised and not recognized by blood group antibodies or by professional phagocytes. Perhaps most surprisingly, treated red blood cells from one species survive much longer than do untreated red blood cells in the circulation of another species.

The invention thus provides for (1) derivatization of human red blood cells to permit transfusions into people difficult to match (because they have pre-existing antibodies to minor blood groups); (2) derivatization of human red blood cells to permit transfusions into people of unknown blood groups who may even differ in major (e.g., ABO) blood groups from the donor; (3) derivatization—by perfusion of mPEG solutions—of human organ grafts to prevent unexpected hyperacute rejection episodes; (4) derivatization—by perfusion of mPEG solutions—of organs from non-human animals to prevent hyperacute rejection and to improve the chances of ultimate successful engraftment in humans.

MATERIALS AND METHODS

Normal red blood cells (erythrocytes) were washed 3× in isotonic saline. A red blood cell suspension of hematocrit ~12% is prepared in isotonic alkaline phosphate buffer (PBS; 50 mM $K_2HPO_4$ and 105 mM NaCl, pH ~9.2). Activated methoxypolyethylene glycol (mPEG; Sigma Chemical Co.) is added and the red cells are incubated for 30 minutes at 4° C. Cell derivatization can also be done under other pH and temperature conditions with comparable results to those presented. For example, red blood cells derivatized at pH 8.0 for 60 minutes at 22° C. demonstrated virtually identical characteristics to those derivatized at pH 9.2 for 30 minutes at 4° C. The extreme range of pH and temperature conditions make this procedure broadly applicable to a wide range of cells and tissues. The proposed mechanism of covalent reaction with external proteins and other membrane components is outlined below. Typical mPEG concentrations used range from 0 to 8 mg per ml of red blood cell suspension. The typical mPEG concentration to be used on other anuclear (i.e., platelets) and various nucleated cells (e.g., vascular endothelial, hepatic, neuronal, pancreatic cells, epithelial cells, etc.) can readily be determined in view of the teachings herein.

EXAMPLE I

Inhibition of Red Blood Cell Agglutination

Figure 3:
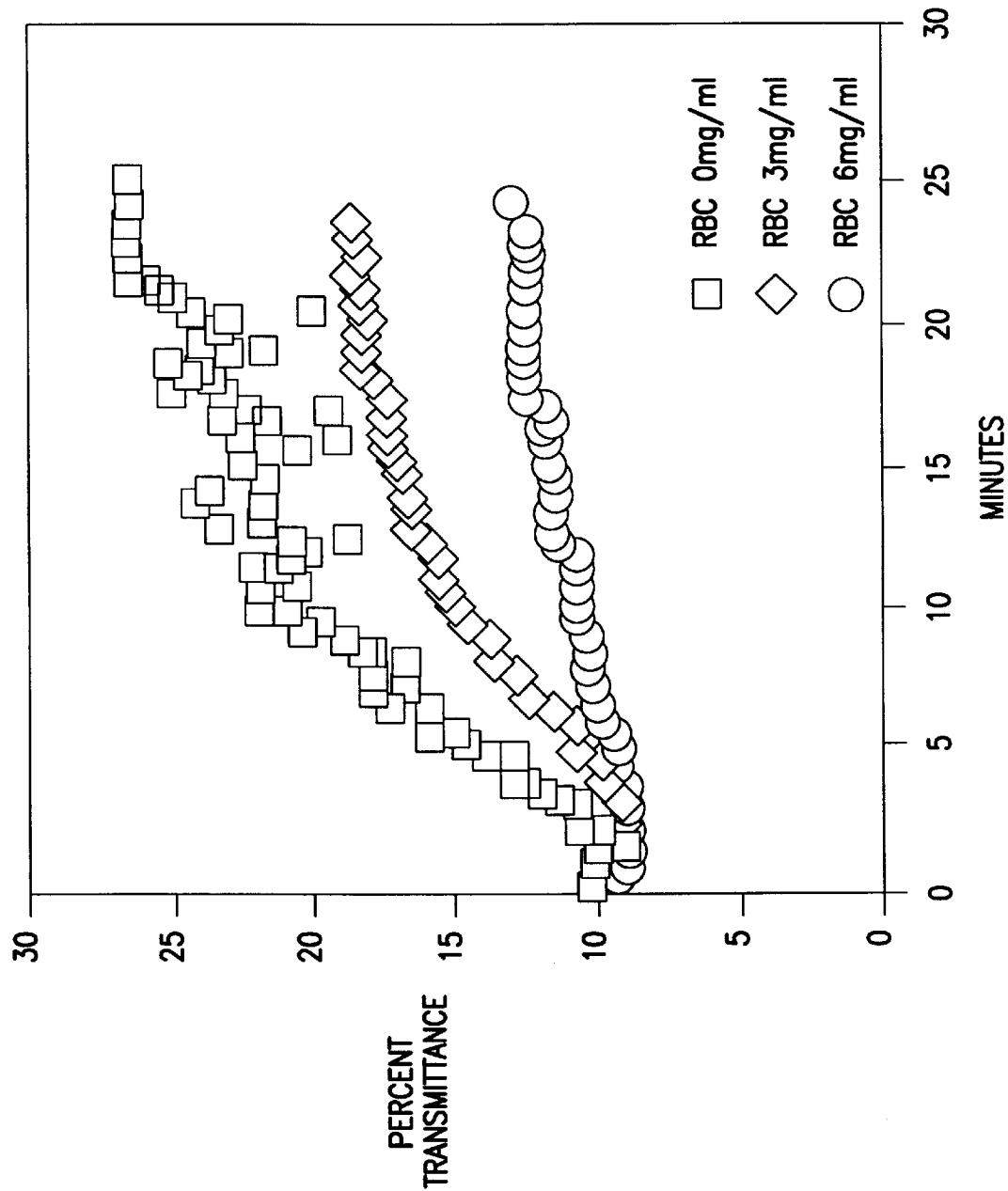

As shown in FIG. 3, the covalent binding of mPEG to the membrane proteins of intact red blood cells prevents red blood cell agglutination. This is apparent at the gross level using agglutination induced by ABO antibodies and at a finer level using a platelet aggregometer modified to measure red blood cell aggregation (FIG. 3). Type A red blood cells were treated with 0, 1, 3, or 6 mg activated mPEG per ml of blood and incubated at 4° C. for 30 minutes. The cells were washed 3 times with isotonic saline and resuspended to a 40% hematocrit in saline. For gross agglutination, equal volumes of a 40% hematocrit and a commercially available anti-A blood typing antibody (Carolina Biological Supply) were mixed and photographed. Increasing amounts of bound mPEG effectively inhibited the agglutination reaction. FIG. 3 shows red blood cell microaggregation as measured at 37° C. in a platelet aggregometer. As shown, mPEG modification caused a dose-dependent inhibition of anti-A antibody induced red blood cell aggregation.

EXAMPLE II

Effect on Red Blood Cell Stability

Figures 4, 5:
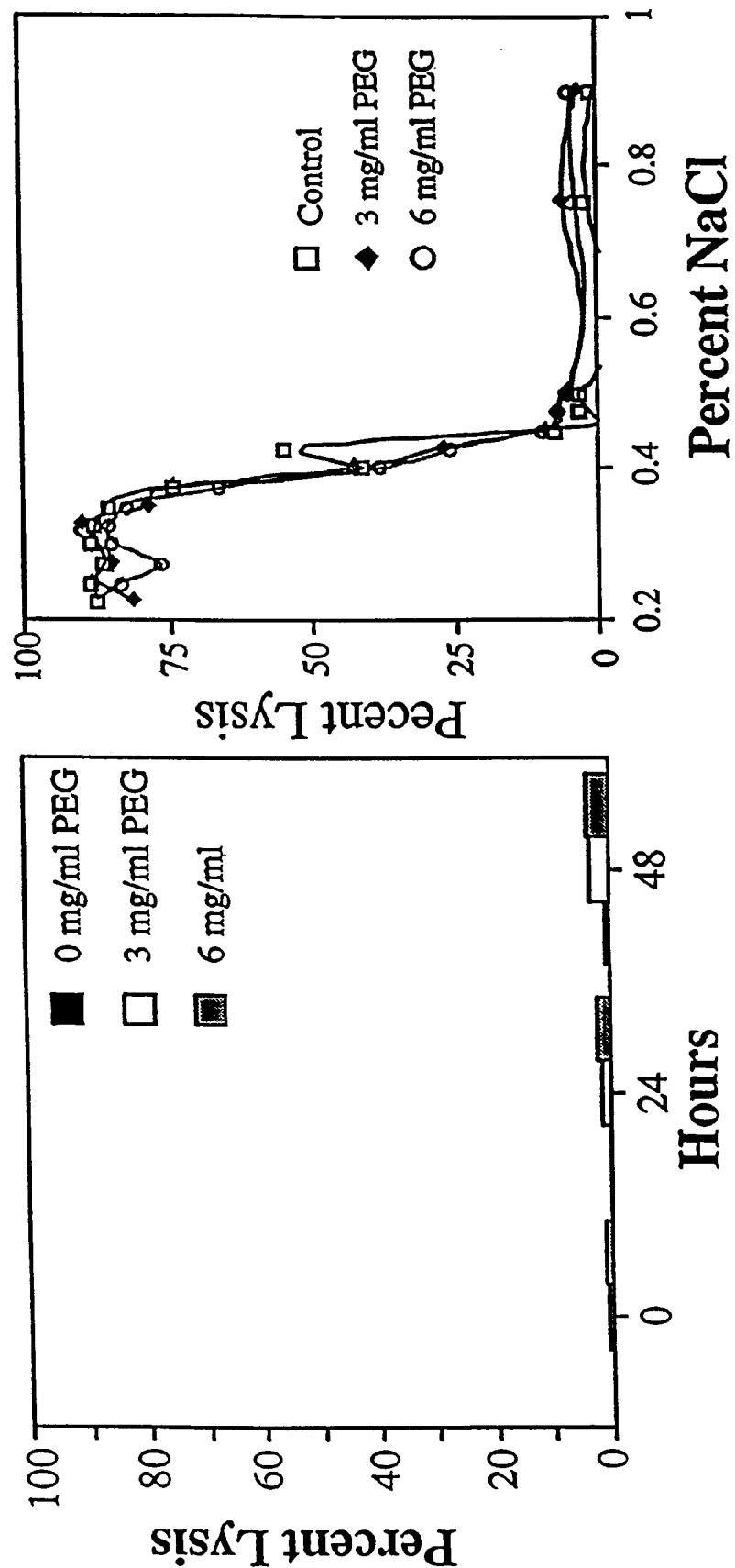

While mPEG-modification of red blood cells slightly increases red blood cell lysis, this lysis is less than 5% of the total red blood cell mass (FIG. 4). Furthermore, mPEG-attachment was found to have no effect on red blood cell osmotic fragility (FIG. 5). Red blood cell stability was minimally modified by the covalent attachment of mPEG. As shown in FIG. 4., red blood cell lysis was slightly increased by the attachment of mPEG. However, red blood cell lysis after 24 hours storage at 4° C. or after incubation at 37° C. was less than 5%. As shown in FIG. 5, osmotic fragility of the mPEG-treated red blood cells was also unaffected. Shown are the osmotic fragility profiles of control and mPEG-modified (3 & 6 mg/ml) red blood cells after 48 hours incubation at 37° C. Again, while a very minor increase in spontaneous lysis was observed, no significant differences in the osmotic lysis profiles were seen.

EXAMPLE III

Figure 6:
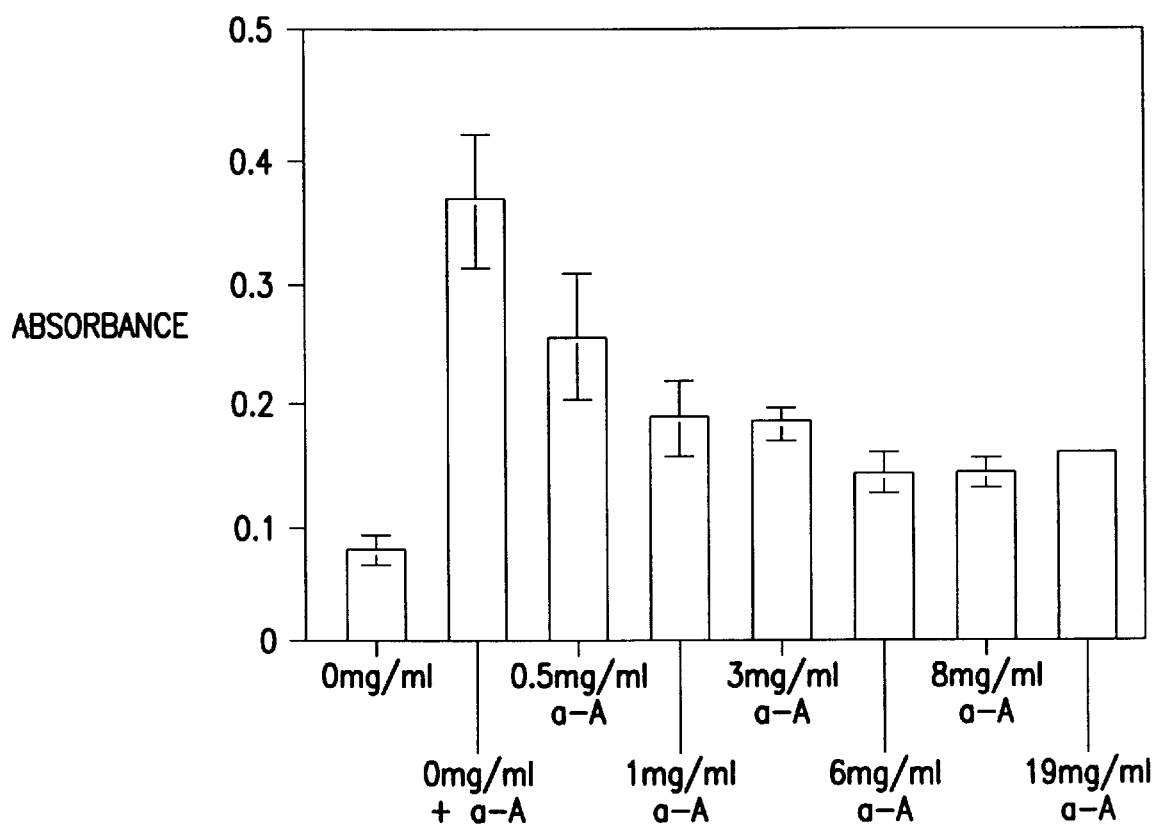

Inhibition of Antibody Binding mPEG-modified red blood cells bind significantly less anti-A antibody (FIG. 6). As shown in FIG. 6, an ELISA assay of mPEG-treated human blood type A⁻ red blood cells demonstrates significantly less antibody binding by mPEG-modified red blood cells. The control and mPEG red blood cells were mixed with an IgG anti-A antibody incubated for 30 minutes. The samples were extensively washed and a secondary antibody (anti-human IgG conjugated with alkaline phosphatase) was added to quantitate bound anti-Blood group A antibody.

EXAMPLE IV

Figure 7:
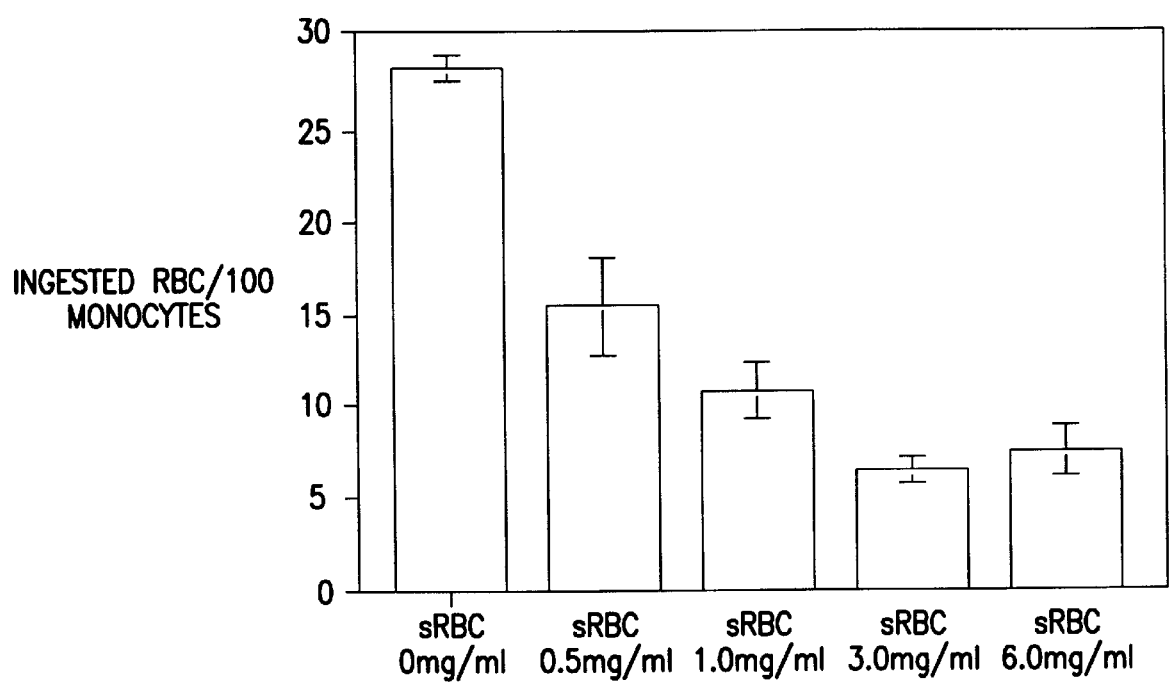

Inhibition of Phagocytosis of Foreign Cells mPEG-modified sheep red blood cells are significantly less prone to phagocytosis by human peripheral blood monocytes (FIG. 7). As would be indicated by decreased antibody binding (FIG. 6), mPEG-modified sheep red blood cells are significantly less susceptible to IgG-mediated phagocytosis by human peripheral blood monocytes. mPEG-modified sheep red blood cells were incubated with human peripheral blood monocytic cells for 30 minutes. The uningested red blood cells were removed by hypotonic lysis and the number of monocytes containing sheep red blood cells, as well as the number of sheep red blood cells ingested, were determined microscopically.

Figure 8:
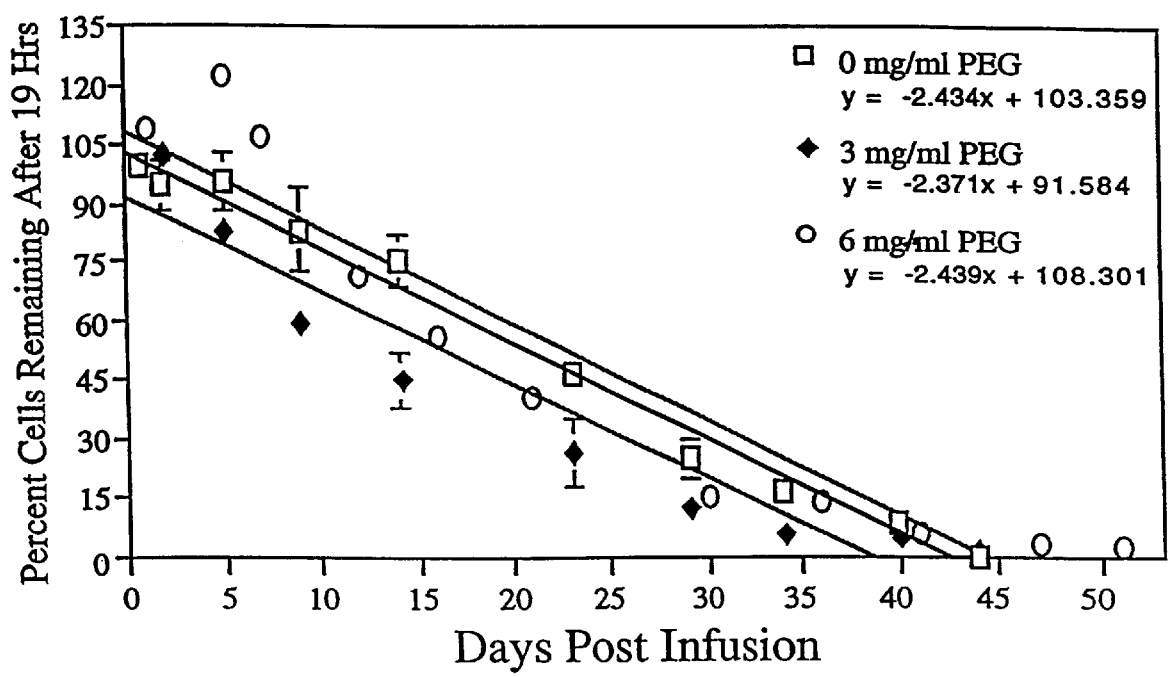

EXAMPLE V mPEG-Derivitized Mouse Red Blood Cells Have Normal In Vivo Survival As shown in FIG. 8, no significant differences were noted in the in vivo survival of control red blood cells and red blood cells modified with either 3 or 6 mg/ml activated mPEG. In vivo survival of control and mPEG-modified mouse red blood cells was determined using a fluorescent fatty acid label (PKH-26; Sigma Chemical Company). Blood was obtained from donor BALB/C mice, treated with 0, 3, or 6 mg/ml activated mPEG and washed thrice. The washed cells were then labeled with PKH-26 and injected i.p. into naive BALB/C mice. Blood samples were obtained by tail-cuts at the indicated time points and analyzed via FACScan.

Figure 9:
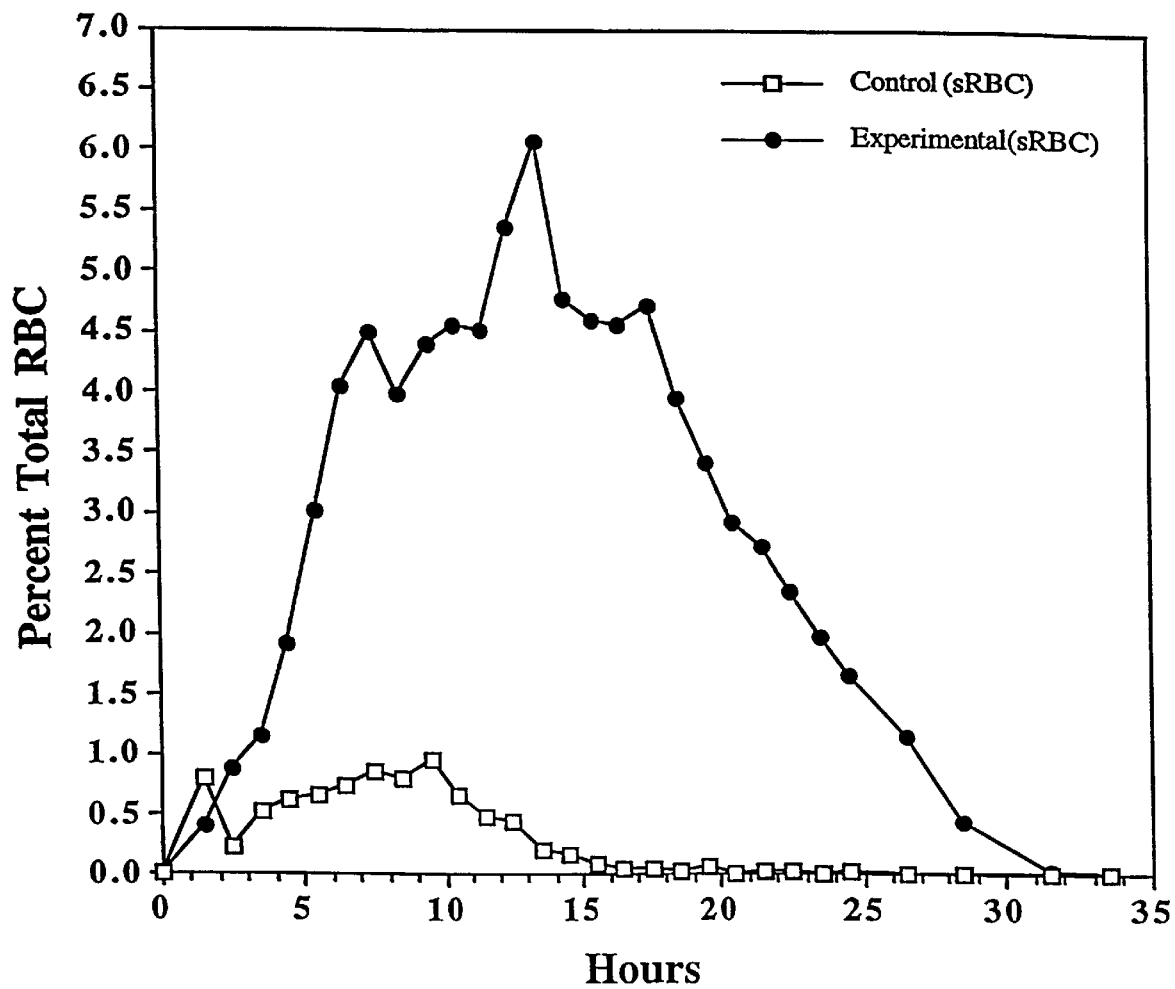

EXAMPLE 6 mPEG-Derivitization of Sheep Red Blood Cells Results in Enhanced In Vivo Survival In Mice Comparable numbers of mPEG-modified sheep red blood cells (mPEG-sRBC) were injected i.p. into BALB/C mice. As shown in FIG. 9, mPEG-sRBC showed a greater rate of entry into the peripheral circulation and demonstrated longer in vivo survival in mice. In vivo survival of mPEG-sRBC in mice was determined using a fluorescent fatty acid label (PKH-26; Sigma Chemical Company). Blood was obtained from a donor sheep and treated with 0 or 6 mg/ml activated mPEG and washed thrice. The washed sheep red blood cells were labeled with PKH-26 and injected i.p. into naive BALB/C mice. Blood samples were obtained by tail-cuts at the indicated time points and analyzed via FACScan.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Abuchowski, A. et al. (1977a) Alteration of immunological properties of bovine serum albumin by covalent attachment of polyethylene glycol. *J. Biol. Chem.,* 252:3578–3581.

Abuchowski, A. et al. (1977b) Effect of covalent attatchment of polyethylene glycol on immunogenicity and circulating life of bovine liver catalase. *J. Biol. Chem.,* 252:3582–3586.

Harris, J. M., et al. (1984) Synthesis and characterization of Poly(ethylene Glycol) Derivatives. *J. Poly. Sci.,* 22:341–352.

Harris, J. M. (1985) Laboratory Synthesis of Polyethylene Glycol Derivatives. *Journal of Macromolecular Sciences Reveiws in Macromolecular Chemistry and Physics.* C25:325–373.

Jackson, C-J. et al. (1987) Synthesis, isolation, and characterization of conjugates of ovalbumin with monomethoxypolyethylene glycol using cyanuric chloride as the coupling agent. *Anal. Biochem.,* 165:114–127.

Klibanov, A. L. et al. (1991) Activity of amphipathic poly(ethylene glycol) 5000 to prolong the circulation time of liposomes depends on the liposome size and is unfacorable for immunoliposome binding to target. *Biochim. Biophys. Acta* 1062:142–148.

Lacy, P. E., et al., (1991) Maintenance of Normoglycemia in Diabetic Mice by Subsutaneous Xenografts of Encapsulated Islets. *Science* 254:1782–1794.

Lasic, D. (1992) Liposomes. *American Scientist,* 80:20–31.

Lim, F., and Sun, A., (1980) Microencapsulated Islets as Bioartificial Endocrine Pancreas. *Science,* 210:908–910.

Maruyama, K. et al. (1992) Prolonged circulation time in vivo of large unilamellar liposomes composed of distearoyl phosphatidylcholine and cholesterol containing amphipathic poly(ethylene glycol). *Biochim. Biophys. Acta.* 1128:44–49.

Merrill, E. W. Poly(Ethylene Oxide) and blood contact: A chronicle of one laboratory. *In: Poly(Ethylene Glycol) Chemistry: Biotechnical and Biomedical Application* (Harris, J. M, Editor) 1992, Pelnum Press, NY. pp. 199–220.

Mitz, M. A., and Summaria, L. J. (1961) Synthesis of biologically active cellulose derivatives of enzymes. *Nature* 189:576–577.

Park, K. D. et al. PEO-Modified Surfaces—In vitro, Ex vivo, and In vivo blood compatibility. *In: Poly(Ethylene Glycol) Chemistry: Biotechnical and Biomedical Application* (Harris, J. M, Editor) 1992, Plenum Press, NY. pp. 283–302.

Sawhney, A. S. et al. (1994) Modification of Islet of Langehans surfaces with immunoprotective poly(ethylene glycol) coatings via interfacial photopolymerization. *Biotech. Bioeng.,* 44:383–386.

Senior, J. et al. (1991) Influence of surfacce hydrophilicity of liposomes on their interaction with plasma protein and clearence from the circulation: studies with poly(ethylene glycol)-coated vesicles. *Biochim. Biophys. Acta.* 1062:77–82.

Vichinsky, E. P., et al. (1990) Alloimmunization in sickle cell anemia and transfusion of racially unmatched blood. *New Eng J Med,* 322:1617–1621.

von Specht, B. -U., et al. (1973) *Hoppe-Seyler's Z. Physiol. Chem.* 354:1659–1660.

Zalipsky, S., and Lee, C., Use of functionalized Poly (Ethylene Glycol)s for modification of polypeptides. *In: Poly(Ethylene Glycol) Chemistry: Biotechnical and Biomedical Application* (Harris, J. M, Editor) 1992, Plenum Press, NY. pp. 347–370.

Poly(Ethylene Glycol) Chemistry: Biotechnical and Biomedical Application. Harris, J. M, Editor. (1992) Plenum Press, NY.

What is claimed is:

1. A non-immunogenic cellular composition comprising:
   a cell having a cell surface and antigenic determinants of said cell surface;
   a linker molecule covalently attached to said cell surface; and
   a non-immunogenic compound covalently attached to said linker molecule and blocking recognition of said antigenic determinants on said cell surface, wherein said cell is a vascular endothelial cell.

2. The cellular composition of claim 1 wherein said non-immunogenic compound is polyethylene glycol.

3. The cellular composition of claim 1 wherein said non-immunogenic compound is methoxypolyethylene glycol.

4. The cellular composition of claim 1 wherein said non-immunogenic compound is polyethylene oxide.

5. The cellular composition of claim 1 wherein said non-immunogenic compound is dextran.

6. The cellular composition of claim 1 wherein said non-immunogenic compound is ficoll.

7. The cellular composition of claim 1 wherein said non-immunogenic compound is arabinogalactan.

8. The cellular composition of claim 1 wherein said linker molecule is cyanuric chloride.

9. The cellular composition of claim 1 wherein said linker molecule is imidazolyl formate.

10. The cellular composition of claim 1 wherein said linker molecule is succinimidyl succinate.

11. The cellular composition of claim 1 wherein said linker molecule is succinimidyl glutarate.

12. The cellular composition of claim 1 wherein said linker molecule is N-hydroxysuccinimide.

13. The cellular composition of claim 1 wherein said linker molecule is 4-nitrophenol.

14. The cellular composition of claim 1 wherein said linker molecule is 2,4,5-trichlorophenol.

15. The cellular composition of claim 1 wherein said linker molecule is covalently attached to said antigenic determinant on said cell surface.

16. The cellular composition of claim 1 wherein said cell is a vascular endothelial cell.

17. A method of producing a non-immunogenic cell, said method comprising:
   covalently attaching a non-immunogenic compound to a linker molecule, and said non-immunogenic compound blocking recognition of antigenic determinants on a cell surface; and
   covalently attaching said linker molecule to a cell surface, so as to produce a non-immunogenic cell, wherein said non-immunogenic cell is a vascular endothelial cell.

18. The method of claim 17 wherein said linker molecule is covalently attached to said antigenic determinant on said cell surface.

19. The method of claim 17 wherein said non-immunogenic cell is a vascular endothelial cell.

20. The method of claim 19 further comprising transplanting a subject with said non-immunogenic cell.

* * * * *